United States Patent [19]

Sanders

[11] Patent Number: 5,709,890
[45] Date of Patent: Jan. 20, 1998

[54] POLYASPARTIC ACID AND ITS ANALOGUES IN COMBINATION WITH INSECTICIDES

[75] Inventor: J. Larry Sanders, Bedford Park, Ill.

[73] Assignee: Donlar Corporation, Bedford Park, Ill.

[21] Appl. No.: 821,037

[22] Filed: Mar. 20, 1997

Related U.S. Application Data

[62] Division of Ser. No. 615,445, Mar. 14, 1996, Pat. No. 5,646,133.

[51] Int. Cl.$^6$ .......... A01N 59/14; A01N 59/22; A01N 27/00; A01N 37/34
[52] U.S. Cl. .......... 424/620; 424/621; 424/622; 424/623; 424/624; 424/625; 424/626; 424/627; 424/628; 424/629; 424/657; 424/658; 424/659; 424/660; 514/12; 514/13; 514/64; 514/65; 514/75; 514/79; 514/86; 514/95; 514/99; 514/102; 514/109; 514/110; 514/112; 514/114; 514/120; 514/121; 514/122; 514/123; 514/125; 514/126; 514/129; 514/131; 514/134; 514/137; 514/139; 514/140; 514/141; 514/142; 514/143; 514/478; 514/479; 514/480; 514/481; 514/482; 514/483; 514/484; 514/485; 514/486; 514/487; 514/488; 514/489; 514/490; 514/504; 514/519; 514/521; 514/531; 514/762; 514/763; 514/766; 514/773
[58] Field of Search .......... 514/12–13, 75, 514/79, 86, 95, 99, 102, 109, 110, 112, 114, 120–123, 125–126, 129, 131, 134, 137, 139–143, 478–490, 773, 65, 64, 519, 521, 531, 504, 762, 763, 766

[56] References Cited

U.S. PATENT DOCUMENTS

| 2,578,652 | 12/1951 | Cassaday | 260/461 |
|---|---|---|---|
| 2,962,521 | 11/1960 | Usui | 260/461 |
| 5,350,735 | 9/1994 | Kinnersley | 504/147 |
| 5,360,892 | 11/1994 | Bonsignore et al. | 528/354 |
| 5,457,176 | 10/1995 | Adler et al. | 538/328 |
| 5,540,927 | 7/1996 | Jason et al. | 424/257 |
| 5,580,840 | 12/1996 | Harms et al. | 504/115 |
| 5,593,947 | 1/1997 | Kinnersley t al. | 504/283 |

FOREIGN PATENT DOCUMENTS

| 5246863 | 9/1993 | Japan . |
|---|---|---|

OTHER PUBLICATIONS

Technological Breakthrough on Fertilizer Use, Agri Finance, Apr. 1993, pp. 16–17.

Kinnersley, et al., Plant Growth Regulation 9, 137–146 (1990).

Calpus Abstract Accession No. 1995: 616583(1995).

WPIDS Abstract Accession No. 93–339638 (1993).

Sinclair, Richard G., "Slow Release Pesticide System ...", Environmental Science & Technology, vol. 7(10), 1973, pp. 955–956.

Turner, D.J. et al., "Complexing Agents as Herbicide Additives," Weed Research, vol. 18, 1978, pp. 199–207.

*Primary Examiner*—John Pak
*Attorney, Agent, or Firm*—Zarley, McKee, Thomte, Voorhees, & Sease

[57] ABSTRACT

An insecticide composition is enhanced from the standpoint of its ability to be absorbed by insects, such as red fire ants, particularly dithiophosphate ester pesticides by the addition of a small amount of a water soluble non-aromatic polyorganic acid or salt form thereof such as polyaspartic acid, particularly preferred with a molecular weight in the range of about 3000 to 40,000.

7 Claims, No Drawings

POLYASPARTIC ACID AND ITS ANALOGUES IN COMBINATION WITH INSECTICIDES

This is a divisional of application Ser. No. 08/615,445 filed on Mar. 14, 1996 which is now U.S. Pat. No. 5,646,133.

BACKGROUND OF THE INVENTION

This invention relates to insecticides. More particularly, in a preferred aspect it relates to an improved method for enhancing effectiveness of dithiophosphate insecticides in absorption by certain insects to effect a kill.

Dithiophosphate insecticides of the type with which the present invention is concerned may be represented by the formula:

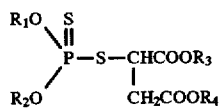

in which $R_1$, $R_2$, $R_3$ and $R_4$ are each an aliphatic or aromatic hydrocarbon radical. Such esters are well known and may be conveniently prepared, for instance, by reacting an O,O-dialkyl dithiophosphate with a dialkyl maleate as described and claimed in U.S. Pat. No. 2,578,652. A typical and well known ester of this class is O,O-dimethyl-S-(1,2-dicarbethoxyethyl)-dithiophosphate which is commercially available as "Malathion®." It is with this latter compound that much of the test experience with the present invention is particularly concerned. The following description does apply to dithiophosphate ester insecticides in general, and as explained later, to a broader class of insecticides as well. Thus, it is to be understood that the present process is equally as applicable to other insecticides besides dithiophosphate esters.

As heretofore mentioned, such dithiophosphate ester insecticides and their preparation are known and have been known and effective for many years. However, their effectiveness against some insects of which red fire ants are but one example, has been somewhat limited at lower concentrations.

Other classic insecticide classes besides the organo phosphates and dithiophosphate esters in particular are also in need of enhanced effectiveness for certain insects. Examples of such other insecticide classes include carbamates, chlorinated hydrocarbons, synthetic pyrethroids, insect growth regulators, botanicals such as nicotine plant derivatives and naturally occurring insecticides such as boron and arsenic compounds. These are all within the scope of the present invention.

Moreover, in order to minimize pollution risks, there are always continuing efforts towards increasing the effectiveness of known insecticides from the standpoint of the ability to achieve the same level of effectiveness, but with less insecticide.

Accordingly, it is a primary objective of the present invention to provide a composition which enhances the effectiveness of certain classic types of insecticides, particularly the preferred dithiophosphate pesticides like Malathion®.

Another objective of the present invention is to achieve enhanced effectiveness of insecticides by enhancing the ability of the insecticide to be absorbed by cell membranes of the exterior cell layers of the insect, thereby substantially increasing the effectiveness and thus allowing reduction of the treatment or dosage level required.

Another objective of the present invention is to provide an insecticide effectiveness enhancing composition which uses as an additive a polluting free additive that is environmentally unobjectionable.

The method and means of accomplishing each of the above objectives will become apparent from the detailed description of the invention which follows.

SUMMARY OF THE INVENTION

An insecticide composition which comprises an insecticide such as a dithiophosphate ester pesticide, particularly Malathion®, in a preferred composition combination with an absorption enhancing effective amount of a water soluble non-aromatic polyorganic acid or salt form of such an acid, particularly polyaspartic acid. The invention in a broader aspect also involves a method of enhancing the dose effectiveness of certain classes of insecticides by adding to those a membrane penetration effectiveness aid, such as polyaspartic acid.

DETAILED DESCRIPTION OF THE INVENTION

The present invention is premised upon the fact that it has been discovered that certain compounds, namely certain polymeric organic amino acids, as set forth in earlier commonly-owned U.S. Pat. No. 5,350,735, which, along with each of its continuation-in-part applications, namely Ser. No. 08/313,436, filed Sep. 27, 1994, which is now U.S. Pat. No. 5,593,947, Ser. No. 08/439,279, filed May 11, 1995, which is now U.S. Pat. No. 5,580,840, and Ser. No. 08/447,784, filed May 23, 1995, which is now U.S. Pat. No. 5,661,103, all of which disclosures are incorporated herein by reference, can be used effectively in enhancing the penetration of dithiophosphate ester insecticides such as Malathion® through the exterior surface cells of an insect, such as red fire ants.

The invention, of course, is not limited to the treatment of red fire ants, but can be used effectively for treating any of the pest insects for any agricultural or horticultural crop, including fruits, cereals, vegetables, flowers and ornamentals. The invention is also useful for any application where insecticides are used for control of insect pests, such as in homes, farm buildings, grain elevators, greenhouses or control of pest insects in the general environment, such as ants, cockroaches, spiders, fleas, house flies and the like, as well as disease bearing and nuisance insects such as mosquitoes, chiggers, black flies, horse flies and the like.

In general, the polymeric organic acid can be simply added to the liquid form of the insecticide, generally within a weight ratio of from 1:100 (polyaspartate:insecticide) to 100:1 (polyaspartate:insecticide).

The polymeric organic acids, to be suitable for the practice of the present invention, must be water soluble, non-aromatic, and must have a molecular weight sufficiently large to preclude absorption into system of plants. To that end, the non-aromatic polymeric organic acid units (residues), or mers, in the linear polymer chain that constitutes the polymeric acid organic acids having a molecular weight in excess of about 100,000 usually exhibit poor solubility in water for the present purposes. Thus, for present purposes a polymeric organic acid molecular weight not larger than about 100,000 is preferred. Particularly, preferred molecular weight is in the range of about 1,500 to about 100,000.

Illustrative are polymeric organic acids, with or without carboxylic acid, thiocarboxylic acid, imidocarboxy, and/or amino side chains such as, for example, polyacrylic acid, polytartaric acid, polymaleic acid, polylysine, polyglutamic acid, polyaspartic acid, polyglycine, polycysteine, polycysteine/glutamic acid, mixtures of the foregoing or their salts, copolymers of the above, and the like. Thus, block or random copolymers or terpolymers of several organic acids are also within the purview of the present invention as the polymeric acid component thereof. For example, the utilized polymeric acid component can be a block copolymer of aspartic acid residues and L-lactic acid residues, a random copolymer of aspartic acid residues and glycolic acid residues, a conjugated protein constituted by amino acid residue chains interconnected by one or more polycarboxylic acid residues, a copolymer of acrylic acid and acrylamide, and the like.

Polymers of organic acids are commercially available. In addition, such polymeric acids, especially poly(amino acids), can be made, inter alia, by thermal condensation methods. See, for example, U.S. Pat. No. 5,057,597 to Koskan, Little et al., American Chemical Society 97:263–279 (1991), and U.S. Pat. No. 4,696,981 to Harada et al.

While the above description has been presented with particular examples of the classic organo phosphate esters such as Malathion®, other insecticides (as earlier mentioned) can be used with the same observed enhanced effectiveness. For example, in the specific working examples below, data is presented for carbamates such as 1-Naphthyl methylcarbamate and as well for Diazinon®.

The insecticide, in combination with the polyorganic acid or salt, such as polyaspartic acid, may be applied by direct spray, dusting, drenching, may be applied in granular form, as a wet powder, an aerosol, by baiting, as an attractant, or it can be broadcast. In short, the application method is not critical.

The following examples are offered to further illustrate, but not necessarily limit the process and to demonstrate the compositions of the present invention as showing enhanced insecticide effectiveness in comparison with the insecticide alone. It will be apparent to those of ordinary skill in the art that certain modifications can be made to the process and composition without departing from the spirit and scope of the invention here described.

EXAMPLE 1

A series of experiments were conducted with Malathion®, which is a dithiophosphate ester insecticide with a formula as hereinbefore described wherein $R_1$ and $R_2$ are methyl, and $R_3$ and $R_4$ are ethyl. It is chemically named O,O,-dimethyl)-S-(1,2 dicarbethoxyethyl)-dithiophosphate. The tests were used for controlling the red imported fire ant. By way of background, the red imported fire ant has migrated throughout the Southern United States and is predicted to continue moving to areas with similar ecological conditions, such as Denver, Colo. Red imported fire ant mounds are a nuisance in home lawns, industrial areas, and agricultural farmland and grazing lands. The red imported fire ant attacks humans, domestic animals and wildlife. The bites or "stings" frequently become infected and have caused blindness in animals and extended discomfort in humans for periods of two weeks and longer. It is therefore desirable to control these ants.

In all of the foregoing experiments, polyaspartic acid refers to a 41% (by weight) solution of sodium polyaspartate, having a molecular weight of between 3000 and 5000, in water. Two solutions of insecticide were prepared. Solution 1 contained 2 Tablespoons per gallon (2TBS/gal) of Malathion® in water. Solution 2 contained 2TBS/gal of Malathion® and 2 TBS/gal of polyaspartic acid. The two solutions were applied on active mounds of red fire ants at ambient temperatures from 80° F. to 85° F.

The purpose of the test was to evaluate a moderately mild insecticide alone and with polyaspartic acid membrane enhancing aids added to the Malathion®.

Ten mounds of active red fire ants were sprayed at ambient temperatures of 80° F. to 85° F. These were treated with Malathion® alone and with Malathion® plus the hereinbefore described polyaspartic acid.

Ratings were made at four hours post-treatment and at 24 hours post-treatment for activity of each mound. A plastic spoon was inserted into and removed from each mound several times in rapid succession to aggravate the ants.

Internal activity of the mounds was evaluated by digging into each mound with a sharp shovel to observe activity and channel configuration. The results are shown in the table below.

| Treatment | Percent Red Imported Fire Ants 4 Hours | Controlled 24 Hours |
|---|---|---|
| MALATHION ® | 0 | 0 |
| MALATHION ® + Polyaspartic Acid 300–500 mw | 99* | 100 |

*only one ant observed; possibly a scout

From the above table it can be seen that polyaspartic acid, when added to the Malathion®, effectively controlled the red imported fire ant, whereas the Malathion® alone provided virtually no control.

When the above was repeated with other insects such as spiders, mites, other ants and bees, similar results are obtained in that kill effectiveness at the same dose level is dramatically enhanced.

EXAMPLES 2–6

The labeled rates of the insecticides used in the following examples are as follows: Malathion®—2 teaspoons per gallon; Diazinon®—2 teaspoons per gallon; Sevin®—1 tablespoon per gallon. Solutions of insecticide, with and without added polyaspartic acid, were prepared. Treatment of insects was accomplished as follows: Prior to introduction of insects, 50 mL of insecticide solution was added to each of several one quart jars. The jars were sealed, shaken, drained and allowed to dry for 2 hours at ambient room temperature.

Red Imported Fire Ants (RIFA) were treated with insecticide Carbamate (1-Naphthyl methylcarbamate), Diazinon® (O,O-dimethyl-O-[6-methyl-2-(1-methylethyl)-4-pyrimidinyl] phosphorothioate) and Malathion® and in combination with Polyaspartates. The ants were placed in sealed containers, and their mortality and knock-down rates were taken over time.

Table 1 shows that there were little differences in mortality of RIFA with a 0.03 labeled rate of Sevin® (1-Naphthyl methylcarbamate) used in combination with 1×(1 TBS/Gal) or 2×(2 TBS/Gal) of Polyaspartates. The percent knock-down (Table 2), however, was significantly increased at the 1 and 2 hour exposure with the 2×Polyaspartates in combination with the 0.03 labeled rate of Sevin®.

Malathion® (0.3 labeled rate), in combination with 1× and 2×Polyaspartates rates significantly increased the mortality of RIFA in one hour as shown in Table 3.

Table 4 shows significant affect of Polyaspartates in combination with a 0.25 labeled rate of Diazinon® applied along at one hour of exposure. At 0.125 labeled rate of Diazinon® the combination of Polyaspartates was significantly more effective on mortality of RIFA (Table 5) at 2 hours. At four hour exposure Diazinon® at the 0.03 labeled rate shows significant increases in mortality of RIFA with a 1× and 2× of polyaspartates rate compared to the insecticide along (Table 6).

TABLE 1

Sevin ® at 0.03 label rate

| Hours | Active | % Mortality |
|---|---|---|
| 2 | insecticide only | 26.1% |
| 2 | insecticide, 1X | 27.1% |
| 2 | insecticide, 2X | 35.1% |

TABLE 2

Sevin ® at 0.03 label rate

| Hours | Active | % Mortality |
|---|---|---|
| 1 | insecticide only | 18.7% |
| 1 | insecticide, 1X | 13.6% |
| 1 | insecticide, 2X | 80.7% |
| 2 | insecticide only | 80.0% |
| 2 | insecticide, 1X | 80.0% |
| 2 | insecticide, 2X | 94.0% |

TABLE 3

Malation ® at 0.3 label rate

| Hours | Active | % Mortality |
|---|---|---|
| 1 | insecticide only | 47.7% |
| 1 | insecticide, 1X | 79.3% |
| 1 | insecticide, 2X | 76.0% |

TABLE 4

Diazinon ® at 0.25 label rate

| Hours | Active | % Mortality |
|---|---|---|
| 1 | insecticide only | 70.8% |
| 1 | insecticide, 2X | 91.0% |

TABLE 5

Diazinon ® at 0.125 label rate

| Hours | Active | % Mortality |
|---|---|---|
| 2 | insecticide only | 53.4% |
| 2 | insecticide, 2X | 69.9% |

TABLE 6

Diazinon ® at 0.03 label rate

| Hours | Active | % Mortality |
|---|---|---|
| 4 | insecticide only | 10.7% |
| 4 | insecticide, 1X | 68.5% |
| 4 | insecticide, 2X | 91.8% |

It therefore can be seen that the invention accomplishes at least all of its stated objectives.

What is claimed is:

1. An insecticide composition which comprises, an insecticide selected from the group consisting of chlorinated hydrocarbons, pyrethroids, natural boron insecticidal compounds, and natural arsenic insecticidal compounds, and a small but insecticide absorption enhancing effective amount of a water soluble, non-aromatic, polyorganic acid or salt thereof which is polyaspartic acid, said polyaspartic acid having a molecular weight larger than 1500.

2. The insecticide composition of claim 1 wherein the polyaspartic acid has a molecular weight in the range of about 1500 to about 100,000.

3. The insecticide composition of claim 2 wherein the polyaspartic acid has a molecular weight in the range of about 3000 to 40,000.

4. A method of enhancing the absorption effectiveness of chlorinated hydrocarbon, pyretheroid, natural boron and natural arsenic insecticides, said method comprising:

adding to an insecticide selected from the group consisting of chlorinated hydrocarbons, pyrethroids, natural boron insecticidal compounds, and natural arsenic insecticidal compounds a small but insecticide absorption enhancing effective amount of a water soluble, non-aromatic polyorganic acid or salt form thereof which is a polyamino acid or a copolymer of said acid, selected from the group consisting of polyaspartic acid, polyglutamic acid, polyglycine, polylysine, a copolymer of cysteine and glutamic acid and a terpolymer of cysteine, glutamic acid and aspartic acid, and salt form thereof, said polyamino acid having a molecular weight larger than 1500.

5. The method of claim 4 wherein the polyamino acid is polyaspartic acid.

6. The method of claim 4 wherein the polyaspartic acid has a molecular weight in the range of about 1500 to about 100,000.

7. The method of claim 4 wherein the polyamino acid is polyaspartic acid having a molecular weight in the range of about 3000 to 40,000.

* * * * *